US009791528B2

(12) United States Patent
Kim et al.

(10) Patent No.: US 9,791,528 B2
(45) Date of Patent: Oct. 17, 2017

(54) MAGNETIC RESONANCE IMAGING SYSTEM AND MAGNETIC RESONANCE IMAGING METHOD

(71) Applicant: Samsung Electronics Co., Ltd., Suwon-si (KR)

(72) Inventors: Young Beom Kim, Yongin-si (KR); Yeunchul Ryu, Hwaseong-si (KR); Jaemock Yi, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 932 days.

(21) Appl. No.: 14/075,753

(22) Filed: Nov. 8, 2013

(65) Prior Publication Data
US 2014/0132261 A1    May 15, 2014

(30) Foreign Application Priority Data

Nov. 14, 2012 (KR) .................. 10-2012-0129092

(51) Int. Cl.
*G01V 3/00* (2006.01)
*G01R 33/483* (2006.01)
*A61B 5/055* (2006.01)
*G01R 33/561* (2006.01)

(52) U.S. Cl.
CPC .......... *G01R 33/4835* (2013.01); *A61B 5/055* (2013.01); *G01R 33/5611* (2013.01)

(58) Field of Classification Search
CPC .............. G01R 33/5608; G01R 33/543; G01R 33/4835; G01R 33/4828; A61B 5/055
USPC ........................................ 324/309
See application file for complete search history.

(56) References Cited

U.S. PATENT DOCUMENTS

| 6,043,654 | A |   | 3/2000  | Liu et al. |
|-----------|---|---|---------|-----------|
| 6,144,383 | A | * | 11/2000 | Lichtenbelt ............ G06T 17/10 345/419 |
| 6,424,153 | B1 | * | 7/2002 | Liu .................. G01R 33/56509 324/307 |

(Continued)

FOREIGN PATENT DOCUMENTS

| EP | 2 219 023 A2 | 8/2010 |
|----|--------------|--------|
| JP | 2004-49753 A | 2/2004 |

(Continued)

*Primary Examiner* — Walter Lindsay, Jr.
*Assistant Examiner* — Frederick Wenderoth
(74) *Attorney, Agent, or Firm* — NSIP Law (57) ABSTRACT

A magnetic resonance imaging (MRI) method includes defining a plurality of sub-volumes so that each of the sub-volumes includes a plurality of sequential slices of a plurality of slices that make up a volume of a subject, wherein the sub-volumes are divided into a plurality of groups so that any neighboring sub-volumes belong to different groups; applying radio-frequency (RF) pulses including a plurality of frequency components and a selection gradient to the subject to simultaneously excite a plurality of sub-volumes in each of the groups; performing three-dimensional (3D) encoding on each of the excited sub-volumes so that only some slices of the plurality of slices in each of the excited sub-volumes are encoded in a slice direction; acquiring magnetic resonance signals from the encoded sub-volumes; and reconstructing the acquired magnetic resonance signals into image data corresponding to each of the plurality of slices in each of the encoded sub-volumes.

17 Claims, 7 Drawing Sheets

(56) References Cited

U.S. PATENT DOCUMENTS

| | | | |
|---|---|---|---|
| 6,505,064 B1* | 1/2003 | Liu | G06T 11/206 324/307 |
| 7,282,917 B1 | 10/2007 | Brau et al. | |
| 7,917,190 B2 | 3/2011 | Mistretta et al. | |
| 8,030,923 B2 | 10/2011 | Yu et al. | |
| 8,049,496 B2 | 11/2011 | Chen et al. | |
| 8,154,289 B2 | 4/2012 | Zelinski et al. | |
| 2008/0059074 A1* | 3/2008 | Wei | G01V 1/34 702/16 |
| 2008/0214926 A1 | 9/2008 | Fukuta | |
| 2010/0085050 A1* | 4/2010 | Dong | G01R 33/243 324/309 |
| 2011/0109312 A1* | 5/2011 | Yamanaka | G01R 33/288 324/309 |
| 2011/0228998 A1 | 9/2011 | Vaidya et al. | |
| 2012/0056620 A1 | 3/2012 | Feinberg et al. | |
| 2014/0111201 A1 | 4/2014 | Kim et al. | |
| 2014/0132264 A1 | 5/2014 | Kim et al. | |

FOREIGN PATENT DOCUMENTS

| | | |
|---|---|---|
| JP | 2004-135887 A | 5/2004 |
| KR | 10-2005-0072500 A | 7/2005 |

\* cited by examiner

FIG. 7

MAGNETIC RESONANCE IMAGING SYSTEM AND MAGNETIC RESONANCE IMAGING METHOD

CROSS-REFERENCE TO RELATED APPLICATIONS

This application claims the benefit of Korean Patent Application No. 10-2012-0129092 filed on Nov. 14, 2012, in the Korean Intellectual Property Office, the disclosure of which is incorporated herein by reference in its entirety for all purposes.

BACKGROUND

1. Field

This disclosure relates to magnetic resonance imaging systems and magnetic resonance imaging methods.

2. Description of Related Art

Magnetic resonance imaging utilizes magnetic fields produced by magnetism to acquire images of biological tissues in a human body. A magnetic resonance imaging system applies a radio-frequency (RF) signal to biological tissues, thereby causing the biological tissues to resonate. The system also applies a gradient magnetic field to biological tissues to obtain spatial information about the biological tissues.

SUMMARY

In one general aspect, a magnetic resonance imaging (MRI) method includes defining a plurality of sub-volumes so that each of the plurality of sub-volumes includes a plurality of sequential slices of a plurality of slices that make up a volume of a subject, wherein the plurality of sub-volumes are divided into a plurality of groups so that any neighboring sub-volumes belong to different groups; applying radio-frequency (RF) pulses including a plurality of frequency components and a selection gradient to the subject to simultaneously excite a plurality of sub-volumes in each of the plurality of groups; performing three-dimensional (3D) encoding on each of the excited plurality of sub-volumes so that only some slices of the plurality of slices in each of the excited plurality of sub-volumes are encoded in a slice direction; acquiring magnetic resonance signals from the encoded plurality of sub-volumes; and reconstructing the acquired magnetic resonance signals into image data corresponding to each of the plurality of slices in each of the encoded plurality of sub-volumes.

The performing of the 3D encoding may include determining a condition for selecting slices that will undergo encoding in the slice direction from the plurality of slices in each of the excited plurality of sub-volumes to satisfy a preset standard; and performing slice direction encoding on slices selected according to the determined condition.

The condition for selecting the slices may be that (1+v× fa)-th slices are selected from the plurality of slices in each of the excited plurality of sub-volumes, wherein fa may be a factor for satisfying the preset standard and may be an integer greater than or equal to 1, and v may be an integer that increases by 1 beginning from 0 until a value of (1+v×fa) reaches a number of the plurality of slices in each of the excited plurality of sub-volumes.

The reconstructing of the acquired magnetic resonance signals into the image data may include reconstructing the acquired magnetic resonance signals into image data corresponding to each of the encoded plurality of sub-volumes; and reconstructing the image data corresponding to each of the encoded plurality of sub-volumes into the image data corresponding to each of the plurality of slices in each of the encoded plurality of sub-volumes.

The reconstructing of the acquired magnetic resonance signals into the image data corresponding to each of the encoded plurality of sub-volumes and the reconstructing of the image data corresponding to each of the encoded plurality of sub-volumes into the image data corresponding to each of the plurality of slices in each of the encoded plurality of sub-volumes may be performed based on channel information of multi-channel receiver coils configured to acquire the magnetic resonance signals.

The plurality of groups may include a first group through an N-th group, the plurality of sub-volumes may be sequentially and cyclically distributed to the first group through the N-th group, and N may be an integer greater than or equal to 2.

The method of claim may further include performing the applying of the RF pulses and the selection gradient to the subject, the performing of the 3D encoding on each of the excited plurality of sub-volumes, the acquiring of the magnetic resonance signals from the encoded plurality of sub-volumes, and the reconstructing of the acquired magnetic resonance signals into image data for all of the plurality of groups to obtain reconstructed image data for all of the plurality of groups; and synthesizing the reconstructed image data for all of the plurality of groups.

In another general aspect, a non-transitory computer-readable storage medium stores a program for controlling a computer to perform the method described above.

In another general aspect, a medical resonance imaging (MRI) method includes applying a predetermined pulse sequence that performs encoding in a slice direction on some slices of a plurality of slices in each of a plurality of sub-volumes that make up a volume of a subject to the subject, wherein the plurality of sub-volumes are divided into a plurality of groups so that any neighboring sub-volumes belong to different groups; reconstructing image data corresponding to each of the plurality of slices in each of the plurality of sub-volumes of one of the plurality of groups; determining whether the applying of the predetermined pulse sequence and the reconstructing of the image data have been performed for all of the plurality of groups; in response to a determination that the applying of the predetermined pulse sequence and the reconstructing of the image data have not been performed for all of the plurality of groups, applying the predetermined pulse sequence and performing the reconstructing of the image data for a next one of the plurality of groups; and in response to a determination that the applying of the predetermined pulse sequence and the reconstructing of the image data have been performed for all of the plurality of groups, combining image data corresponding to each of the plurality of slices in each of the plurality of sub-volumes of each of the plurality of groups to create a three-dimensional (3D) volume image of the subject.

The predetermined pulse sequence may include a slice direction encoding gradient for encoding only the some slices of the plurality of slices in each of the plurality of sub-volumes; and the some slices may comply with a condition for satisfying a preset standard.

The reconstructing of the image data may include reconstructing the acquired magnetic resonance signals into image data corresponding to each of the plurality of sub-volumes; and reconstructing the image data corresponding to each of the plurality of sub-volumes into image data corresponding to each of the plurality of slices in each of the plurality of sub-volumes of the one group.

The reconstructing of the acquired magnetic resonance signals into the image data corresponding to each of the plurality of sub-volumes and the reconstructing of the image data corresponding to each of the plurality of sub-volumes into the image data corresponding to each of the plurality of slices in each of the plurality of sub-volumes of the one group may be performed based on channel information of multi-channel receiver coils configured to acquire the magnetic resonance signals.

In another general aspect, a non-transitory computer-readable storage medium stores a program for controlling a computer to perform the method described above.

In another general aspect, a magnetic resonance imaging (MRI) system includes an MRI scanner configured to define a plurality of sub-volumes so that each of the plurality of sub-volumes includes a plurality of sequential slices of slices that make up a volume of a subject, wherein the plurality of sub-volumes are divided into a plurality of groups so that any neighboring sub-volumes belong to different groups; apply radio-frequency (RF) pulses including a plurality of frequency components and a selection gradient to the subject to simultaneously excite a plurality of sub-volumes in each of the plurality of groups; perform three-dimensional (3D) encoding on each of the excited plurality of sub-volumes so that only some slices of the plurality of slices in each of the excited plurality of sub-volumes are encoded in a slice direction; and acquire magnetic resonance signals from the encoded plurality of sub-volumes; and a data processor configured to reconstruct the acquired magnetic resonance signals into image data corresponding to each of the plurality of slices in each of the encoded plurality of sub-volumes.

The MRI scanner may be further configured to, as part of the performing of the 3D encoding, determine a condition for selecting slices that will undergo encoding in the slice direction from the plurality of slices in each of the excited plurality of sub-volumes to satisfy a preset standard; perform slice direction encoding on slices selected according to the determined condition.

The condition for selecting the slices may be that (1+v× fa)-th slices are selected from the plurality of slices in each of the excited plurality of sub-volumes, wherein fa may be a factor for satisfying the preset standard and may be an integer greater than or equal to 1, and v may be an integer that increases by 1 beginning from 0 until a value of (1+v×fa) reaches a number of the plurality of slices in each of the excited plurality of sub-volumes.

The data processor may be further configured to reconstruct the acquired magnetic resonance signals into image data corresponding to each of the encoded plurality of sub-volumes; and reconstruct the image data corresponding to each of the encoded plurality of sub-volumes into image data corresponding to each of the plurality of slices in each of the encoded plurality of sub-volumes.

The reconstructing of the acquired magnetic resonance signals into the image data corresponding to each of the encoded plurality of sub-volumes and the reconstructing of the image data corresponding to each of the encoded plurality of sub-volumes into the image data corresponding to each of the plurality of slices in each of the encoded plurality of sub-volumes may be performed based on channel information of multi-channel receiver coils configured to acquire the magnetic resonance signals.

The MRI scanner may include gradient coils configured to apply a first encoding gradient in a first direction, a second encoding gradient in a second direction, and a frequency encoding gradient in a third direction to the subject to perform the 3D encoding on each of the excited plurality of sub-volumes; the second direction may be the slice direction; and the second encoding gradient may encode only the some slices of the plurality of slices in each of the excited plurality of sub-volumes.

The MRI scanner may be further configured to perform the applying of the RF pulses and the selection gradient to the subject, the performing of the 3D encoding on each of the excited plurality of sub-volumes, and the acquiring of the magnetic resonance signals from the excited plurality of sub-volumes to obtain magnetic resonance signals for all of the plurality of groups; and the data processor may include a reconstructor configured to perform the reconstructing of the acquired magnetic resonance signals into image data corresponding to each of the plurality of slices in each of the encoded plurality of sub-volumes for all of the plurality of groups to obtain reconstructed image data for all of the plurality of groups; and a synthesizer configured to synthesize the reconstructed image data for all of the plurality of groups.

Other features and aspects will be apparent from the following detailed description, the drawings, and the claims.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

Figure 1:
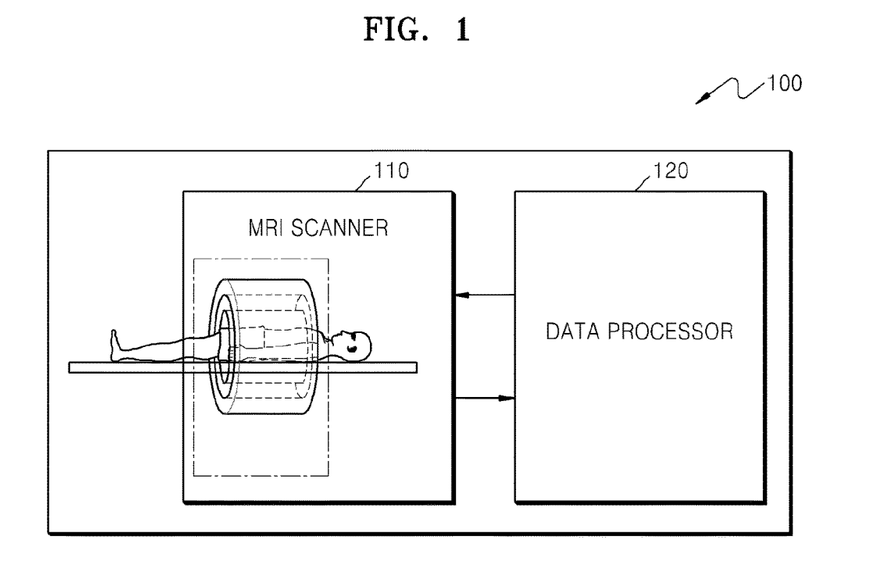
FIG. 1 illustrates an example of a magnetic resonance imaging (MRI) system.

FIG. 1 illustrates an example of a magnetic resonance imaging (MRI) system 100. Referring to FIG. 1, the MRI system 100 includes an MRI scanner 110 and a data processor 120.

Although FIG. 1 only shows components of the MRI system 100 related to this example, it will be readily apparent to one of ordinary skill in the art that the MRI system 100 may also include other common components.

The MRI system 100 non-invasively acquires images containing information about biological tissues of a subject. For example, the MRI system 100 may be a device that utilizes a magnetic field to obtain diagnostic images of a subject, but is not limited thereto. Examples of the subject may include a human body, brain, spine, heart, liver, and fetus, but are not limited thereto. The MRI system 100 may also be a hybrid MRI system combined with other medical equipment, such as a positron emission tomography (PET) device.

The MRI scanner 110 acquires magnetic resonance signals from a plurality of sub-volumes in a volume of the subject. Each of the plurality of sub-volumes may include a predetermined number of slices. The number of slices may be determined automatically according to the properties of the subject and a usage environment, or manually by a user. Likewise, a thickness of the slices may be determined automatically according to the properties of the subject and a usage environment, or manually by the user.

The MRI scanner 110 uses slices in a volume of a subject to define a plurality of sub-volumes, wherein each sub-volume includes at least two sequential slices. For example, when a volume of the subject is composed of 100 slices, the MRI scanner 110 may define 10 sub-volumes, each containing 10 sequential slices. Since a plurality of sub-volumes may be set using slices that are determined automatically according to the properties of the subject and a usage environment, or manually by the user, the MRI scanner 110 may provide a resolution suitable for the usage environment or the user's purposes.

The MRI scanner 110 also applies radio-frequency (RF) pulses including a plurality of frequency components and a selection gradient to the subject to simultaneously excite sub-volumes in each of at least two groups, wherein the plurality of sub-volumes are divided into the at least two groups so that neighboring sub-volumes belong to different groups. The MRI scanner 110 then performs three-dimensional (3D) encoding on each of the excited plurality of sub-volumes so that only some of the slices in each of the excited plurality of sub-volumes are encoded in a slice direction, and acquires magnetic resonance signals from the excited plurality of sub-volumes.

More specifically, when the MRI scanner 110 applies RF pulses containing a plurality of frequency components and a selection gradient to a subject lying in a static magnetic field, a plurality of sub-volumes in each of at least two groups are simultaneously excited. The sub-volumes are divided into the at least two groups so that any neighboring sub-volumes belong to different groups. When the at least two groups include a first group through N-th group, the plurality of sub-volumes in the volume of the subject are sequentially and cyclically distributed to one of the first through N-th groups. N is an integer that is equal to or greater than 2. For example, if the plurality of sub-volumes have first through S-th sub-volumes, the plurality of sub-volumes may be sequentially included in the first through N-th groups. The first sub-volume may be in the first group, the second sub-volume may be in the second group, and the N-th sub-volume may be in the N-th group. The N+1-th, N+2-th, and 2N-th sub-volumes are respectively distributed to the first, second, and N-th groups in a cyclic fashion. By doing so, each of the first through S-th sub-volumes may be grouped in such a way that any neighboring sub-volumes belong to different groups.

The first through S-th sub-volumes in the subject may be sequentially defined based on a direction in which a selection gradient is applied to the subject. For example, in this direction, the first and last sub-volumes may be set to the first and S-th sub-volumes, respectively. When a volume of the subject is defined with respect to x, y, and z-axes, the direction in which the selection gradient is applied may be a z-axis, but is not limited thereto. For example, the x-axis may represent a direction of a sagittal plane or a coronal plane, and the z-axis may represent a direction of an axial plane, or a transverse plane, or a slice direction.

Examples of a plurality of sub-volumes defined using slices in a volume of a subject and at least two groups created by dividing the plurality of sub-volumes so that adjacent sub-volumes are in different groups will now be described with reference to FIGS. 2A and 2B.

Figure 2A:
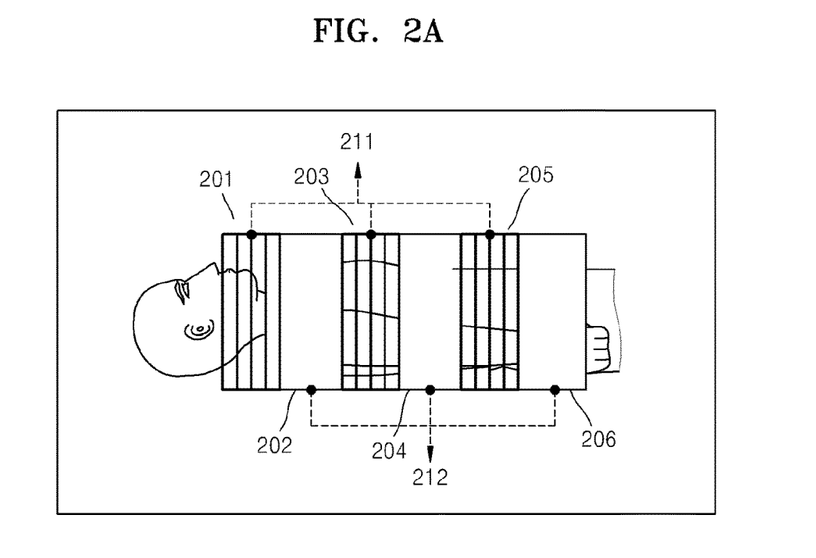
FIGS. 2A and 2B illustrate examples of a method of defining a plurality of sub-volumes using a plurality of slices and a method of grouping the plurality of sub-volumes.
Figure 2B:
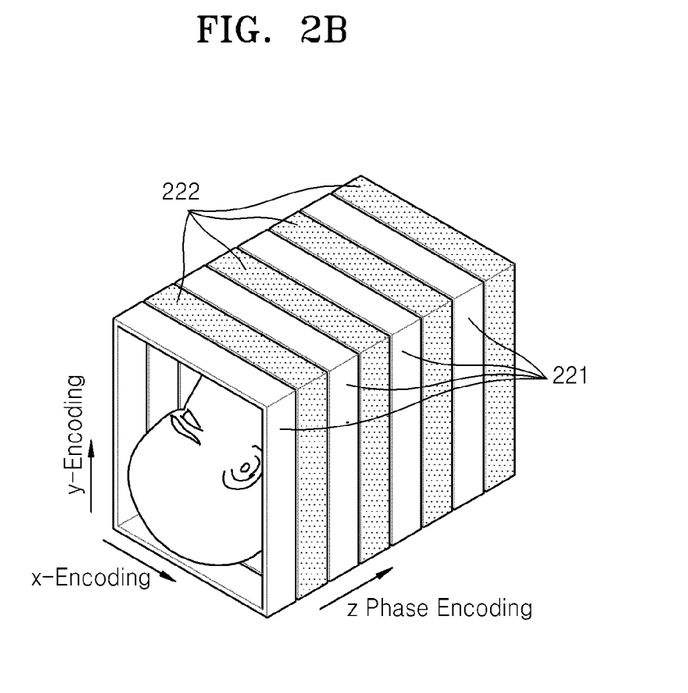

FIGS. 2A and 2B illustrate examples of a method of defining a plurality of sub-volumes using a plurality of slices and a method of grouping the plurality of sub-volumes. Referring to FIGS. 2A and 2B, the MRI scanner 110 applies RF pulses containing a plurality of frequency components and a selection gradient to a subject to simultaneously excite a plurality of sub-volumes in a first one of at least two groups.

For example, when M sub-volumes are simultaneously excited, the applied RF pulses may be multi-band RF pulses generated by modulating a single volume-selective RF pulse into M RF pulses.

As another example, the applied RF pulses may be RF spatial encoding pulses generated by a Hadamard encoding or a phase-offset multiplanar volume imaging technique that excites designated M sub-volumes.

Thus, each of the RF pulses may have a frequency offset, and the RF pulses may be defined by the following Equation 1:

$$\Psi(t) = A \Sigma_m \text{sinc}(\gamma GDt) e^{i\gamma Gd(m)t} e^{i\phi(m)} \quad (1)$$

In Equation 1, $\Psi(t)$ denotes RF pulses, A denotes a constant, m denotes an m-th sub-volume of the M sub-volumes, $\gamma$ denotes a gyromagnetic ratio, G denotes a gradient, D denotes a thickness of sub-volumes, d(m) denotes a position of the m-th sub-volume, $\phi(m)$ denotes a phase of the m-th sub-volume, and t denotes time.

For example, the gradient G may be about 1 kHz/cm, but is not limited thereto. The RF pulses may be frequency modulated to have a frequency offset.

To realize a frequency offset, for example, the MRI scanner 110 may apply RF pulses containing frequency components corresponding to Larmor frequencies of sub-volumes in a first group to a subject located in a static magnetic field while applying a selection gradient to the subject with respect to a predetermined axial direction.

The Larmor frequency refers to a precession frequency of a magnetic moment of atomic nuclei. Atomic nuclei possess magnetic moments or magnetic dipole moments due to their spin. In the absence of an external magnetic field, atoms have magnetic moments arranged in random directions. Conversely, when atoms are placed in a static magnetic field, the atomic nuclei align with the static magnetic field, dropping to a lower energy state. As the atomic nuclei spin, their magnetic moments undergo precessional motion at a frequency called a Larmor frequency. For example, the Larmor frequency may be determined by a product of a gyromagnetic ratio an a strength of an externally applied magnetic field.

The MRI scanner 110 applies a selection gradient to the subject lying in a static magnetic field to distribute a magnetic field whose intensity varies linearly in a predetermined direction. The MRI scanner 110 also applies to the subject RF pulses containing frequency components corresponding to Larmor frequencies of a plurality of sub-volumes to simultaneously excite the plurality of sub-volumes in the first group.

To perform 3D encoding on each of the plurality of sub-volumes excited by the application of the RF pulses and the selection gradient to the subject, the MRI scanner 110 applies to the subject a gradient for performing encoding in a slice direction on only some slices in each of the plurality of sub-volumes. For example, to perform 3D encoding, the MRI scanner 110 may apply a first encoding gradient in a first direction, a second encoding gradient in a second direction, and a frequency encoding gradient in a third direction to the subject, but the MRI scanner 110 is not limited thereto. The second direction may be the same as the direction in which the selection gradient is applied, a slice direction, or a z-axis direction. Thus, the second encoding gradient may be a slice encoding gradient or a slice-direction encoding gradient, and the first encoding gradient may be a phase encoding gradient. The second encoding gradient may be applied to encode only some of the slices in each of the excited plurality of sub-volumes. The first encoding gradient, the second encoding gradient, and the frequency encoding gradient may be applied to the subject to provide information about locations in y-axis, z-axis, and x-axis directions, respectively. The first and second encoding gradients are then used to perform encoding in y-axis and z-axis directions. Encoding in the z-axis direction will be described in detail below with reference to FIG. 3.

Furthermore, to satisfy a preset standard, the MRI scanner 110 determines a condition for selecting slices that will undergo slice-direction encoding from a plurality of slices in each of the excited plurality of sub-volumes, and performs 3D encoding by performing phase encoding in a slice direction on the slices selected according to the determined condition.

For example, a condition for selecting slices that will undergo slice-direction encoding is that (1+v×fa)-th slices are selected from the plurality of slices in each of the plurality of sub-volumes. fa is an acceleration factor for satisfying the preset standard, and is an integer greater than or equal to 1. v is an integer that increases by 1 beginning from 0 until a value of (1+v×fa) reaches a number of the plurality of slices in each of the plurality of sub-volumes. Slice-direction encoding for different acceleration factors will be described in detail below with reference to FIG. 4.

Upon applying the frequency encoding gradient to the subject, the MRI scanner 110 may also read out magnetic resonance signals from the plurality of sub-volumes. The frequency encoding gradient may be a readout gradient. For example, the MRI scanner 110 may apply a readout gradient to the subject to sample magnetic resonance signals. A gradient in the direction in which a selection gradient is applied may not be applied during the application of the readout gradient to the subject, but the MRI scanner 110 is not limited thereto. When the selection gradient is applied in a z-axis direction, the readout gradient may be applied in an x-axis direction.

The MRI scanner 110 then performs 3D encoding on each of the excited plurality of sub-volumes so that only some of the slices in each of the excited plurality of sub-volumes are encoded in a slice direction, and acquires magnetic resonance signals from each of the excited plurality of sub-volumes. The excited plurality of sub-volumes may be sub-volumes in the first group that are excited by RF pulses or a selection gradient. For example, the MRI scanner 110 may use multi-channel receiver coils to obtain magnetic resonance signals. The magnetic resonance signals may be obtained using the readout gradient.

The data processor 120 reconstructs the magnetic resonance signals acquired from the MRI scanner 110 into image data corresponding to each of the excited plurality of sub-volumes. The data processor 120 also reconstructs the image data into other image data corresponding to respective slices in the excited plurality of sub-volumes. Furthermore, the image data corresponding to the excited plurality of sub-volumes and the image data corresponding to the slices may be reconstructed using channel information of multi-channel receiver coils, but the reconstruction is not limited thereto.

For example, the data processor 120 may use a parallel imaging algorithm that takes into consideration channel information of multi-channel receiver coils to reconstruct magnetic resonance signals into image data corresponding to each of a plurality of sub-volumes or each of a plurality of slices. The channel information may represent the coil sensitivity of each of the multi-channel receiver coils. The data processor 120 is not limited thereto, and the data processor 120 may use a parallel imaging algorithm using information about current elements of an RF coil to reconstruct magnetic resonance signals into image data.

More specifically, magnetic resonance signals from the respective multi-channel receiver coils have information about a plurality of sub-volumes and a plurality of slices superimposed on each other. Thus, the data processor 120 may employ a parallel imaging algorithm using channel information of the multi-channel receiver coils to separate the superimposed information and reconstruct image data corresponding to each of the plurality of slices.

These parallel imaging algorithms may include Sensitivity Encoding (SENSE), Generalized Autocalibrating Partially Parallel Acquisitions (GRAPPA), Simultaneous Acquisition of Spatial Harmonics (SMASH), and Partially Parallel Imaging with Localized Sensitivities (PILS), all of which are well known to one of ordinary skill in the art, and thus will not be described in detail here.

The data processor 120 uses de-aliasing in the parallel imaging algorithm and channel information of multi-channel receiver coils to separate the superimposed magnetic resonance signals and reconstruct image data corresponding to each of the plurality of slices.

The MRI system 100 allows simultaneous excitation of a plurality of sub-volumes in a first one of at least two groups created by dividing the plurality of sub-volumes so that adjacent sub-volumes are in different groups, thereby providing a high-speed MRI scan and delivering high resolution 3D volume images at a high signal-to-noise ratio (SNR).

The MRI system 100 also performs slice-direction encoding on only some of the plurality of slices, thereby decreasing an MRI scan time and preventing motion blur, motion artifacts, and other artifacts from occurring due to a long scan time. Thus, the MRI system 100 may be used in Functional MRI or Diffusion Tensor MRI applications.

The MRI system 100 using 3D volume imaging may exhibit higher signal characteristics than 2D slice imaging. Furthermore, the MRI system 100 employs a parallel imaging algorithm in a slice direction to implement high-speed, high-resolution 3D MRI imaging.

FIGS. 2A and 2B illustrate examples of a method of defining a plurality of sub-volumes using a plurality of slices and a method of grouping the plurality of sub-volumes. Referring to FIGS. 2A and 2B, the plurality of slices in a volume of a subject are used to define the plurality of sub-volumes. For example, a first sub-volume 201 may be defined to have four slices assigned sequentially beginning from a first slice. A second sub-volume may also have four slices assigned sequentially beginning from a fifth slice. In this way, the plurality of slices may be used to define the plurality of sub-volumes. Each of the plurality of sub-volumes may include the same number of slices, but are not limited thereto, and some or all of the plurality of sub-volumes may include different numbers of slices. For convenience of explanation, FIGS. 2A and 2B show that the plurality of sub-volumes in the volume of the subject are partitioned into two groups so that adjacent sub-volumes belong to a different group, but they may be partitioned into three or more groups.

Referring to FIG. 2A, the plurality of sub-volumes are divided into first and second groups 211 and 212 each having three sub-volumes. Although each of the sub-volumes in the first or second group 211 or 212 includes four slices, the sub-volumes are not limited thereto, and may include at least two slices.

Excitation of sub-volumes including a plurality of slices as described above may prevent omission of image information due to an inter-slice gap between neighboring slices that may occur in a 2D MRI technique that excites slices having an inter-slice gap between the slices.

Referring to FIG. 2A, first, third, and fifth sub-volumes 201, 203, and 205 may be included in the first group 211 in a z-axis direction, and second, fourth, and sixth sub-volumes 202, 204, and 206 may be included in the second group 212 in the z-axis direction. The MRI scanner 110 in FIG. 1 applies RF pulses and a selection gradient to the subject so that the plurality of sub-volumes 201, 203, and 205 in the first group 211 are simultaneously excited. After completing reconstruction of image data for the first group 211, the MRI scanner 110 applies RF pulses and a selection gradient to the subject so that the plurality of sub-volumes 202, 204, and 206 in the second group 212 are simultaneously excited.

More specifically, the MRI scanner 110 applies first RF pulses and a first selection gradient to the subject so that the plurality of sub-volumes 201, 203, and 205 in the first group 211 are simultaneously excited. The first RF pulses may include a plurality of frequency components, i.e., first through third frequency components for exciting the first, third, and fifth sub-volumes 201, 203, and 205, respectively.

In the same manner, the MRI scanner 110 applies second RF pulses and a second selection gradient to the subject so that the plurality of sub-volumes 202, 204, and 206 in the second group 212 are simultaneously excited.

Referring to FIG. 2B, a plurality of sub-volumes are divided into first and second groups 221 and 222 each having four sub-volumes. First, third, fifth, and seventh sub-volumes are included in the first group 221 in the z-axis direction, and second, fourth, sixth, and eighth sub-volumes are included in the second group 222 in the z-axis direction. When the MRI scanner 110 applies a first encoding gradient in a first direction and a second encoding gradient in a second direction to the subject to perform 3D encoding, the first and second directions may be y- and z-axis directions, respectively.

Simultaneous excitation of the plurality of sub-volumes and encoding of some of the plurality of slices in the second direction as described above may decrease the amount of time required to encode in the second direction. Furthermore, the number of encoding steps in the second direction may be reduced proportionally to the product of the number of sub-volumes in each group and an acceleration factor. As shown in FIG. 2B, each of the first and second groups 221 and 222 includes four sub-volumes. When an acceleration factor fa is used, the number of encoding steps in the z-axis direction may be reduced to $1/(4 \times fa)$ compared to when no grouping is performed and the acceleration factor is not used. Due to its reduced scan time, the MRI system 100 may create high-resolution 3D full-volume images at high speed.

Figure 3:
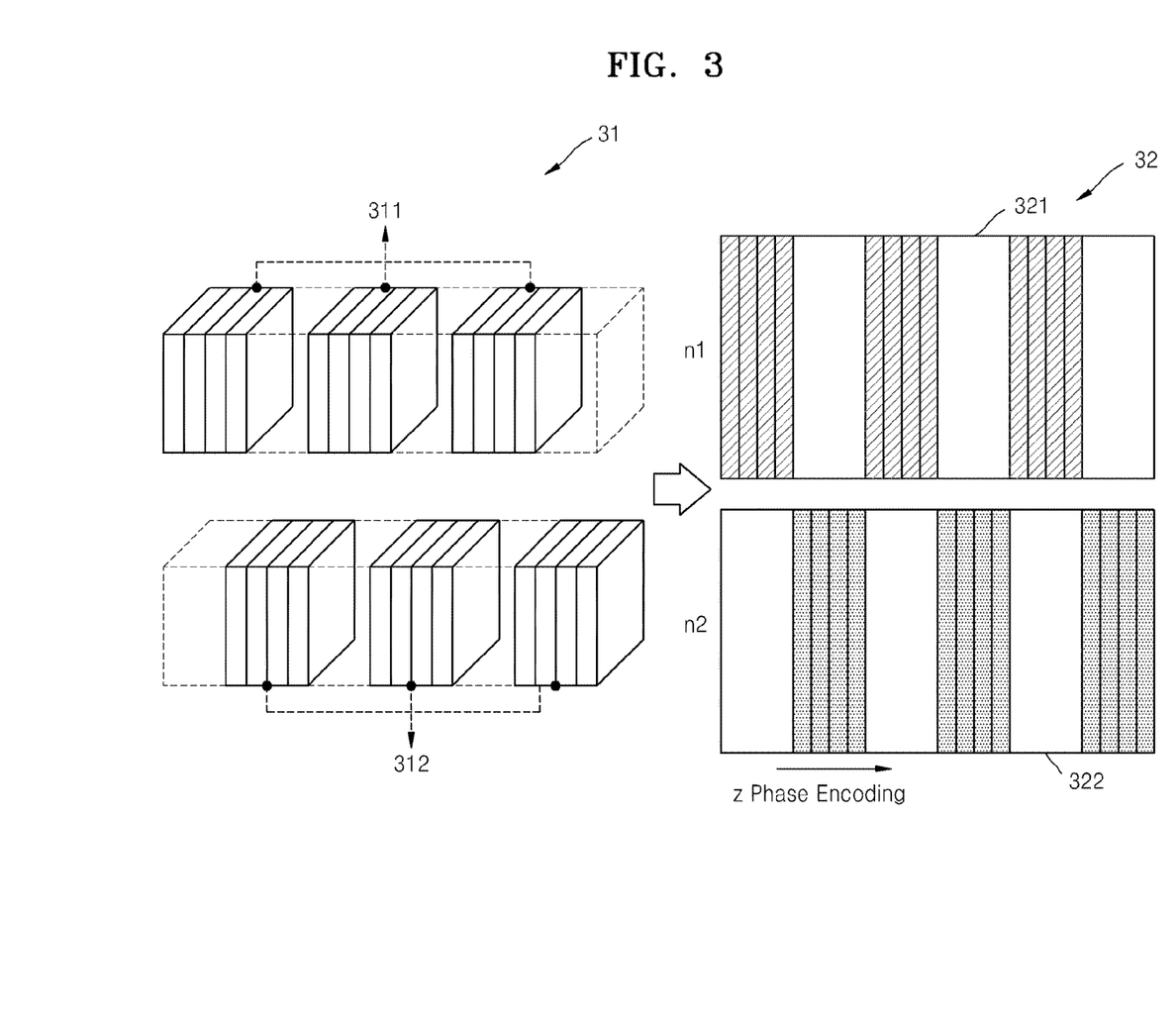
FIG. 3 illustrates an example of a multi-volume imaging technique for each of a plurality of groups.

FIG. 3 illustrates an example of a multi-volume imaging technique for each of a plurality of groups. Referring to section 31 in FIG. 3 in which a plurality of sub-volumes are divided into first and second groups 311 and 312 for simultaneous excitation, a plurality of sub-volumes in the first group 311 are simultaneously excited, and then a plurality of sub-volumes in the second group 312 are simultaneously excited. When the number of groups is n, and the number of simultaneously excited sub-volumes in each group is M, the entire volume of a subject is partitioned into $M \times n$ sub-volumes to perform 3D MRI on the subject. Referring to FIG. 3, since each of the first and second groups 311 and 312 includes three sub-volumes, 3D MRI is performed on the subject that is partitioned into six sub-volumes because $M=3$, $n=2$, and $M \times n=3 \times 2=6$.

Section 32 in FIG. 3 illustrates encoding 321 of a first group 311 in the z-axis direction and encoding 322 of a second group 312 in the z-axis direction.

It is assumed herein that frequency encoding, phase encoding, and slice encoding are performed in x-, y-, and z-axis directions, respectively. When a plurality of sub-volumes in a subject are not partitioned into a plurality of groups, and the number of slice encoding steps in the z-axis direction for the whole volume of the subject is Nz, the number of slice encoding steps in the z-axis direction is Nz. However, because the MRI system 100 in FIG. 1 performs 3D MRI by dividing the whole volume into $M \times n$ sub-volumes, the number of slice encoding steps in the z-axis direction is Nz/M. The number of slice encoding steps in the z-axis direction for each of the $M \times n$ sub-volumes is $Nz/(M \times n)$. The slice encoding is performed simultaneously for the M sub-volumes in each group. Thus, the number of slice encoding steps for each of the n groups is $Nz/(M \times n)$, and the total number of slice encoding steps for all of the n groups is $(Nz/(M \times n)) \times n = Nz/M$.

More specifically, when a plurality of sub-volumes in a subject are not divided into a plurality of groups, the number of phase encoding steps for the whole volume in the y-axis direction is Ny, and the number of slice encoding steps for the whole volume in the z-axis direction is Nz, so the total scan time TA for the whole volume is $Ny \times Nz$. However, when the MRI system 100 is used, the total scan time TA is $Ny \times (Nz/M) = (Ny \times Nz)/M = TA/M$.

The number of encoding steps and the total scan time in the above-described MRI system 100 are the minimum number of encoding steps and the minimum total scan time in the MRI system 100. However, in certain situations, it may not be possible to achieve these minimums. For example, if there are overlapping areas between the plurality of sub-volumes, the number of slice encoding steps in the z-axis direction may be greater than Nz/M, thus increasing the total scan time.

Furthermore, when encoding in a slice direction is performed on only some of the plurality of slices using an acceleration factor fa in the MRI system 100, the total scan time TA for the whole volume of the subject is $TA/(M \times fa)$.

As described above, the MRI system 100 performs 3D encoding by simultaneously exciting sub-volumes each including a plurality of slices, thereby reducing the number of slice encoding steps in the z-axis direction, thereby reducing the scan time required to acquire the whole volume image of the subject. Furthermore, 3D encoding is performed on each sub-volume, thereby eliminating the need to perform MRI scans in a plurality of orientations to remove a gap between slices when 2D encoding is performed on each slice.

Figure 4:
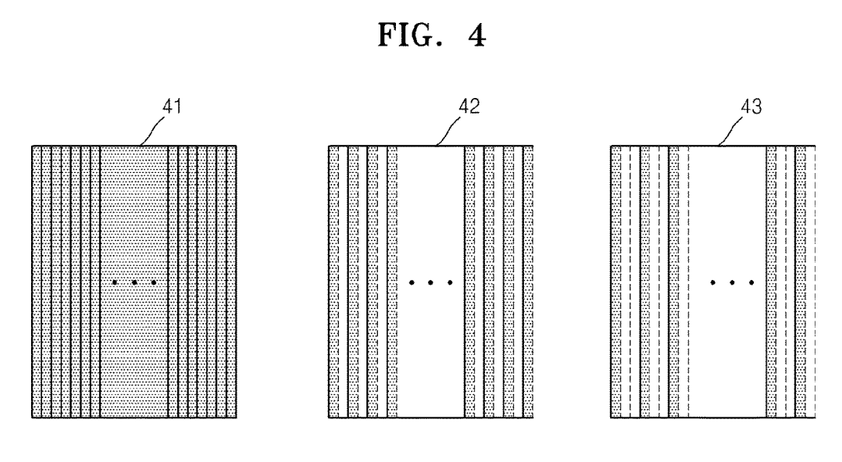
FIG. 4 illustrates examples of encoding in a slice direction according to acceleration factors.

FIG. 4 illustrates examples of encoding in a slice direction according to acceleration factors. While for convenience of explanation, (1+v×fa)-th slices are selected from a plurality of slices to perform slice-direction encoding and the number of slices in each of sub-volumes 41 through 43 is α, the encoding in the slice direction is not limited thereto. An acceleration factor fa may be set to an integer greater than or equal to 1 to satisfy a preset standard. For example, if the preset standard is a scanning speed, a user may set the desired scanning speed using an input apparatus (not shown in FIG. 4, but shown in FIG. 5 as discussed below), and the MRI scanner 110 may determine the acceleration factor fa to satisfy the preset scanning speed. As the acceleration factor fa increases, the scanning speed is increased. Alternatively, the user may directly set the acceleration factor fa through the input apparatus.

The variable v in an integer that increases by 1 beginning from 0 until the value of (1+v×fa) reaches the number a of the plurality of slices in each of the excited plurality of sub-volumes.

The MRI scanner 110 performs 3D encoding by encoding only the (1+v×fa)-th slices of the plurality of slices in each excited plurality of sub-volumes in a slice direction.

While FIG. 4 shows encoding of each of the sub-volumes 41 through 43 according to acceleration factors, the encoding technique may be applied in the same manner to each of a plurality of sub-volumes in each of a plurality of groups.

Referring to FIG. 4, when an acceleration factor fa of 1 is used for the sub-volume 41, the MRI scanner 110 performs encoding in a slice direction for all slices in the sub-volume 41. When the preset scanning speed is satisfied despite slice-direction encoding being performed for all of the number a of slices, the MRI scanner 110 may determine the acceleration factor fa to be 1.

When an acceleration factor fa of 2 is used for the sub-volume 42, shaded slices denote slices undergoing slice-direction encoding, and unshaded slices with dotted lines denote slices not undergoing slice-direction encoding. For example, the MRI scanner 110 may perform slice-direction encoding on first, third, fifth, . . . , (1+2n)-th slices in the sub-volume 42.

Similarly, when an acceleration factor fa of 3 is used for the sub-volume 43, the MRI scanner 110 may perform slice-direction encoding on first, fourth, seventh, . . . , (1+3n)-th slices in the sub-volume 43.

Since the number of slice-direction encoding steps is reduced to 1/fa as described above, the MRI scanner 110 may adjust the acceleration factor fa to provide a scanning speed desired by the user.

Figure 5:
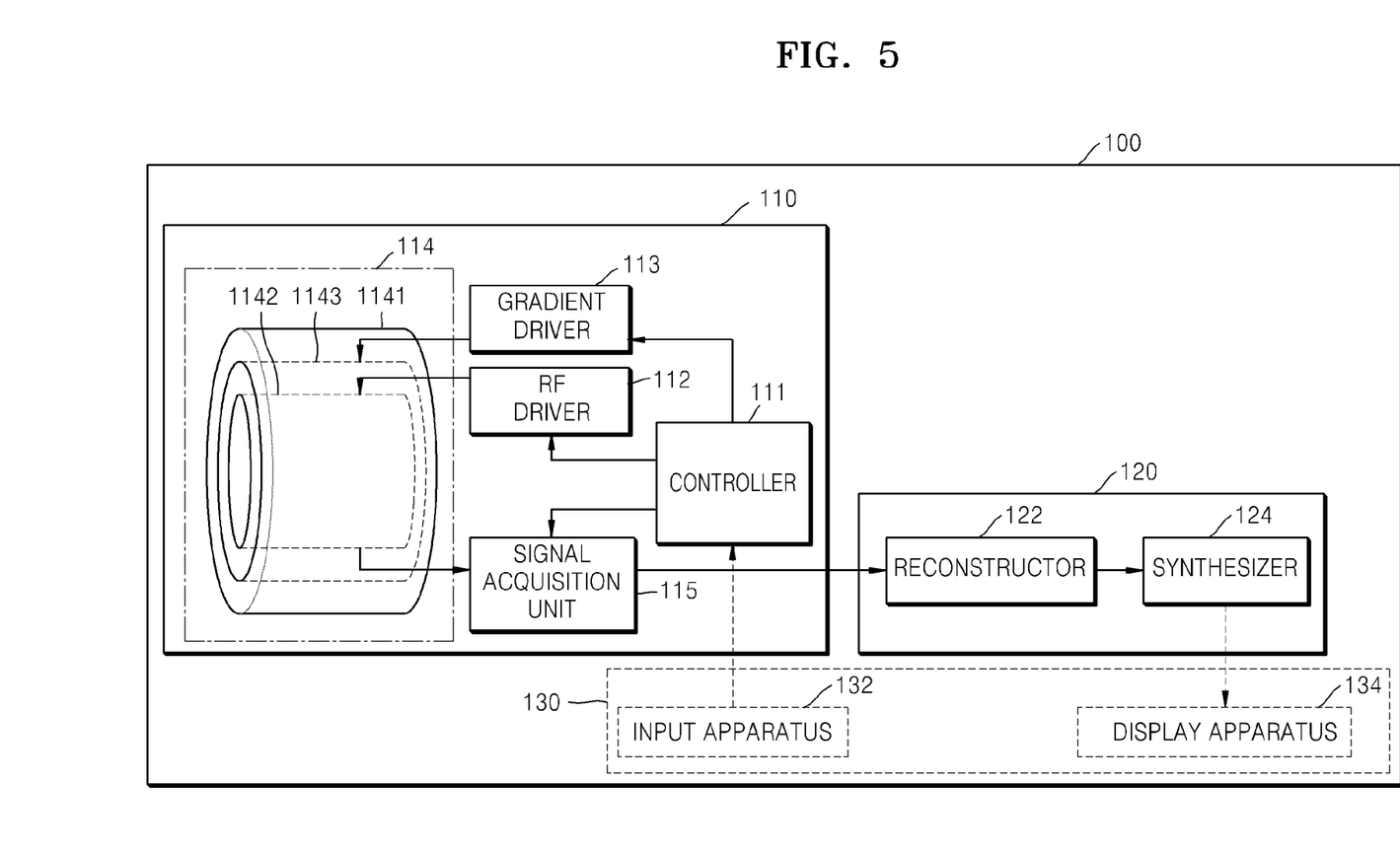
FIG. 5 illustrates another example of an MRI system.

FIG. 5 illustrates another example of an MRI system 100. Referring to FIG. 5, the MRI system 100 includes an MRI scanner 110, a data processor 120, and a user interface 130. The MRI scanner 110 includes a controller 111, an RF driver 112, a gradient driver 113, a magnet apparatus 114, and a signal acquisition unit 115. The magnet apparatus 114 includes a magnetic force generator 1141, RF coils 1142, and gradient coils 1143. The data processor 120 includes a reconstructor 122 and a synthesizer 124. The user interface 130 includes an input apparatus 132 and a display apparatus 134. The MRI system 100 of FIG. 5 is a more detailed example of the MRI system 100 of FIG. 1. Thus, the descriptions with respect to the MRI system 100 in FIG. 1 are also applicable to the descriptions of the MRI system 100 in FIG. 5, and thus are not repeated here.

The MRI system 100 non-invasively acquires images containing information about biological tissues of a subject. The images may be 3D volume images, but are not limited thereto. The MRI scanner 110 applies a predetermined pulse sequence to the subject to obtain magnetic resonance signals emitted by the subject. The predetermined pulse sequence may perform encoding in a slice direction on some of a plurality of slices in each of a plurality of sub-volumes that make up a volume of the subject.

The controller 111 controls the overall operation of the MR scanner 110, and controls the MR scanner 110 to perform an MRI scan according to a scanning speed, an acceleration factor, or a resolution. For example, the controller 111 controls the RF driver 112, the gradient driver 113, and the signal acquisition unit 115. The RF driver 112 drives the RF coils 1142, and the gradient driver 113 drives the gradient coils 1143.

The magnet apparatus 114 applies RF pulses and a gradient to the subject and acquires magnetic resonance signals from the subject. The magnet apparatus 114 may be located within a shielded space, or be open to the outside.

The magnetic force generator 1141 produces a magnetic force so that the subject is located in a static magnetic field.

The RF coils 1142 apply RF pulses containing a plurality of frequency components to the subject and acquire magnetic resonance signals from the subject. The RF coils 1142 may include both RF transmitter coils and RF receiver coils, or RF transceiver coils that both transmit and receive. Hereinafter, for convenience of explanation, the RF coils 1142 are described as having both the RF transmitter coils and the RF receiver coils, but are not limited thereto.

RF pulses applied by the RF transmitter coils of the RF coils 1142 may include multi-band RF pulses or spatial encoding RF pulses. The RF receiver coils of the RF coils 1142 acquire magnetic resonance signals from the subject and output the acquired signals to the data processor 120. The RF receiver coils may be multi-channel receiver coils. For example, the RF receiver coils may be multi-channel receiver coils containing 32 channels, but are not limited thereto.

The gradient coils 1143 apply a selection gradient, a first encoding gradient, a second encoding gradient, and a frequency encoding gradient to a subject. For example, the gradient coils 1143 may include z coils for applying the selection gradient and the second encoding gradient, x coils for applying the frequency encoding gradient, and y coils for applying the first encoding gradient.

The signal acquisition unit 115 acquires the magnetic resonance signals output from the RF coils and performs predetermined operations on the acquired magnetic resonance signals. For example, the signal acquisition unit 115 may include an amplifier for amplifying the acquired magnetic resonance signals, a demodulator for demodulating the amplified magnetic resonance signals, and an analog-to-digital converter (ADC) for converting the demodulated magnetic resonance signals into digital form. The signal acquisition unit 115 may further include a storage unit for storing the digital magnetic resonance signals.

The data processor 120 performs predetermined operations on the magnetic resonance signals received from the MRI scanner 110.

The reconstructor 122 reconstructs the received magnetic resonance signals into image data corresponding to each of a plurality of sub-volumes.

For a reconstruction operation, the reconstructor 122 uses the magnetic resonance signals from the MRI scanner 110 to make up a k-space and performs Fourier transformation on k-space data in the k-space. The k-space data has image data for a plurality of sub-volumes and a plurality of slices all superimposed on each other.

More specifically, multi-channel receiver coils receive magnetic resonance signals for superimposed images of an excited plurality of sub-volumes. The reconstructor 122 uses channel information of the multi-channel receiver coils to separate magnetic resonance signals for the superimposed images into image data corresponding to each of the plurality of slices.

A parallel imaging algorithm is a technique for de-aliasing or removing aliasing caused due to a reduction in sampling lines for signal acquisition to increase the scanning speed. For example, the parallel imaging algorithms may include SENSE, which uses coil field sensitivity corresponding to channel information of each multi-channel receiver coil, and GRAPPA, which uses an auto-calibration signal (ACS) kernel to estimate a value of an unacquired signal line from acquired magnetic resonance signals for surrounding signal lines. The reconstructor 122 uses channel information of multi-channel receiver coils and de-aliasing in a parallel imaging algorithm to reconstruct the superimposed magnetic resonance signals into image data corresponding to each of the plurality of slices, as described in greater detail below with reference to FIG. 7.

The synthesizer 124 synthesizes the reconstructed image data provided by the reconstructor 122. Synthesis may mean fusion or combining. As described above, for example, when the subject consists of first and second groups, the MRI scanner 110 first applies RF pulses containing a plurality of frequency components and a selection gradient to the subject so that a plurality of sub-volumes in the first group are simultaneously excited. The MRI scanner 110 then performs 3D encoding on each of the excited plurality of sub-volumes so that only some of the slices in each of the excited plurality of sub-volumes are encoded in a slice direction and acquires magnetic resonance signals from the plurality of sub-volumes. The reconstructor 122 reconstructs the magnetic resonance signals into image data corresponding to each of the plurality of slices in the first group. The MRI scanner 110 then repeats this process for a plurality of sub-volumes in the second group to acquire magnetic resonance signals from the plurality of sub-volumes in the second group, and the reconstructor 122 reconstructs the magnetic resonance signals into image data corresponding to each of the plurality of slices in the second group. The synthesizer 124 combines image data corresponding to each of the plurality of slices in the first group with the image data corresponding to each of the plurality of slices in the second group and creates a whole volume image of the subject.

The user interface 130 obtains input information from the user and displays output information. While FIG. 5 shows that the input apparatus 132 is separated from the display apparatus 134 for convenience of explanation, the user interface 130 is not limited thereto. In other words, the input apparatus 132 and the display apparatus 134 may be integrated into a single device for operation.

The input apparatus 132 obtains input information for selecting a resolution of an MR image, a scanning speed, an acceleration factor, and a thickness of slices from the user. The display apparatus 134 displays the whole volume image of the subject created by the synthesizer 124 or an image of a region of interest in the whole volume image. Although the MRI system 100 includes the display apparatus 134, the display apparatus 134 may be disposed outside of the MRI system 100.

Figure 6:
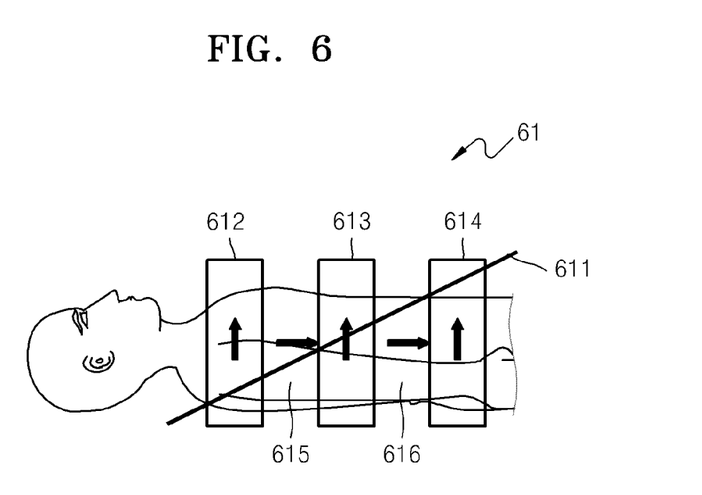
FIG. 6 illustrates an example of simultaneous excitation of a plurality of sub-volumes.

FIG. 6 illustrates an example of simultaneous excitation of a plurality of sub-volumes. According to a multi-volume imaging technique 61, upon application of a selection gradient to a subject lying in a static magnetic field, a linearly varying magnetic field gradient 611 is created in the subject so that each of a plurality of sub-volumes 612 through 616 in the subject has a different Larmor frequency.

When a first sub-volume 612, a third sub-volume 613, and a fifth sub-volume 614 are in a first group, RF pulses having a plurality of frequency components for exciting the first, third, and fifth sub-volumes 612 through 614 are applied to the subject to simultaneously excite the first, third, and fifth sub-volumes 612 through 614 in the first group. For example, the first, third, and fifth sub-volumes 612 through 614 may be excited by RF pulses having first, third, and fifth Larmor frequencies, respectively.

Figure 7:
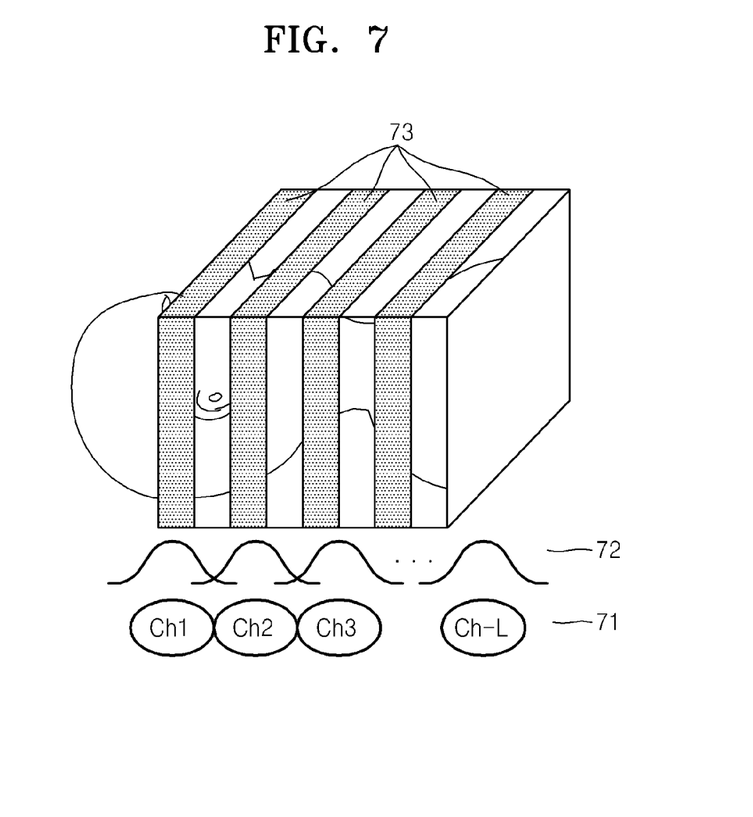
FIG. 7 illustrates an example of reconstruction of image data.

FIG. 7 illustrates an example of reconstruction of image data. Referring to FIG. 7, reference numeral 71 denotes multi-channel RF receiver coils having L channels, and reference numeral 72 denotes respective coil field maps for the multi-channel RF receiver coils. The coil field maps 72 may be sensitivity profiles of the multi-channel RF receiver coils 71. When a plurality of sub-volumes in a first group 73 are simultaneously excited, the multi-channel RF receiver coils 71 acquire magnetic resonance signals from the plurality of sub-volumes in the first group 73.

When S denotes signals received from multi-channel RF receiver coils 71 containing 32 channels, B denotes coil field maps for the respective multi-channel RF receiver coils 71, and F denotes signals representing reconstructed image data for the plurality of sub-volumes in the first group 73, the relationship between S, B, and F is given by Equations 2 and 3 below.

$$S = (bR)F = BF \qquad (2)$$

In Equation 2, b is a sensitivity profile of each of the multi-channel RF receiver coils 71, and R is phase information about each of the plurality of sub-volumes in the first group 73 when RF pulses containing a plurality of frequency components are applied to each of the plurality of sub-volumes.

For example, first through third sub-volumes in the first group 73 may be excited by RF pulses having first through third Larmor frequencies. Similarly, the remaining sub-volumes in the first group 73 may be excited by different Larmor frequencies. As evident from Equation 2, B representing the coil field maps 72 may be defined by the product of phase information R about RF pulses and the sensitivity profile b of each of the multi-channel RF receiver coils 71.

However, when the RF pulses having a plurality of frequency components have the same phase, the coil field maps 72 may be defined without considering the phase information R of the RF pulses. In this case, an identity matrix may be used as the phase information R of Equation 2.

$$\begin{bmatrix} S_0 \\ S_1 \\ S_2 \\ \vdots \\ S_{31} \end{bmatrix} = \begin{bmatrix} B_0^0 & \cdots & B_0^3 \\ B_1^0 & \cdots & B_1^3 \\ B_2^0 & \cdots & B_2^3 \\ \vdots & & \vdots \\ B_{31}^0 & \vdots & B_{31}^3 \end{bmatrix} \begin{bmatrix} f^0 \\ f_1 \\ f^2 \\ f^3 \end{bmatrix} \quad (3)$$

In Equation 3, $S_p$ denotes a signal received from a p-th channel coil of the multi-channel RF receiver coils 71, $B_p^m$ denotes a coil field map for an m-th sub-volume of the plurality of sub-volumes in the first group 73 and the p-th channel coil, and $f^m$ denotes image data for the m-th sub-volume.

The reconstructor 122 in FIG. 5 performs operations using Equation 4 below to reconstruct magnetic resonance signals received from the multi-channel RF receiver coils 71 into image data corresponding to each of the plurality of sub-volumes in the first group 73.

$$F = (B^T \cdot B)^{-1} \cdot B^T \cdot S \quad (4)$$

In Equation 4, $B^T$ denotes the transpose of the B matrix.

As described above, the reconstructor 122 uses channel information of the multi-channel receiver coils 71 and de-aliasing in a parallel imaging algorithm to reconstruct the superimposed magnetic resonance signals into image data corresponding to each of the plurality of sub-volumes.

After being received from the multi-channel RF receiver coils 71, magnetic resonance signals superimposed in a k-space may be separated using RF decoding exploiting coil sensitivities of the multi-channel RF receiver coils 71.

Image data corresponding to each of the plurality of sub-volumes is reconstructed from the magnetic resonance signals, and may be again reconstructed into image data corresponding to each of a plurality of slices in each of the plurality of sub-volumes using coil sensitivities of the multi-channel RF receiver coils 71.

In slice direction encoding, since only some of the plurality of slices in each sub-volume are encoded in a slice direction, there may be an overlap of information between slices in the reconstructed image data corresponding to each of the plurality of sub-volumes. Thus, to unfold overlapping information between slices, the data processor 120 may utilize the coil sensitivities of the multi-channel RF receiver coils 71. Since the unfolding process is similar to the reconstruction of image data corresponding to the plurality of sub-volumes, a detailed description thereof will be omitted.

As described above, the MRI system 100 removes or prevents aliasing artifacts caused by simultaneous excitation of a plurality of sub-volumes and folding artifacts due to slice direction encoding of only some of the plurality of sub-volumes, thereby reconstructing image data corresponding to each of the plurality of sub-volumes.

Figure 8:
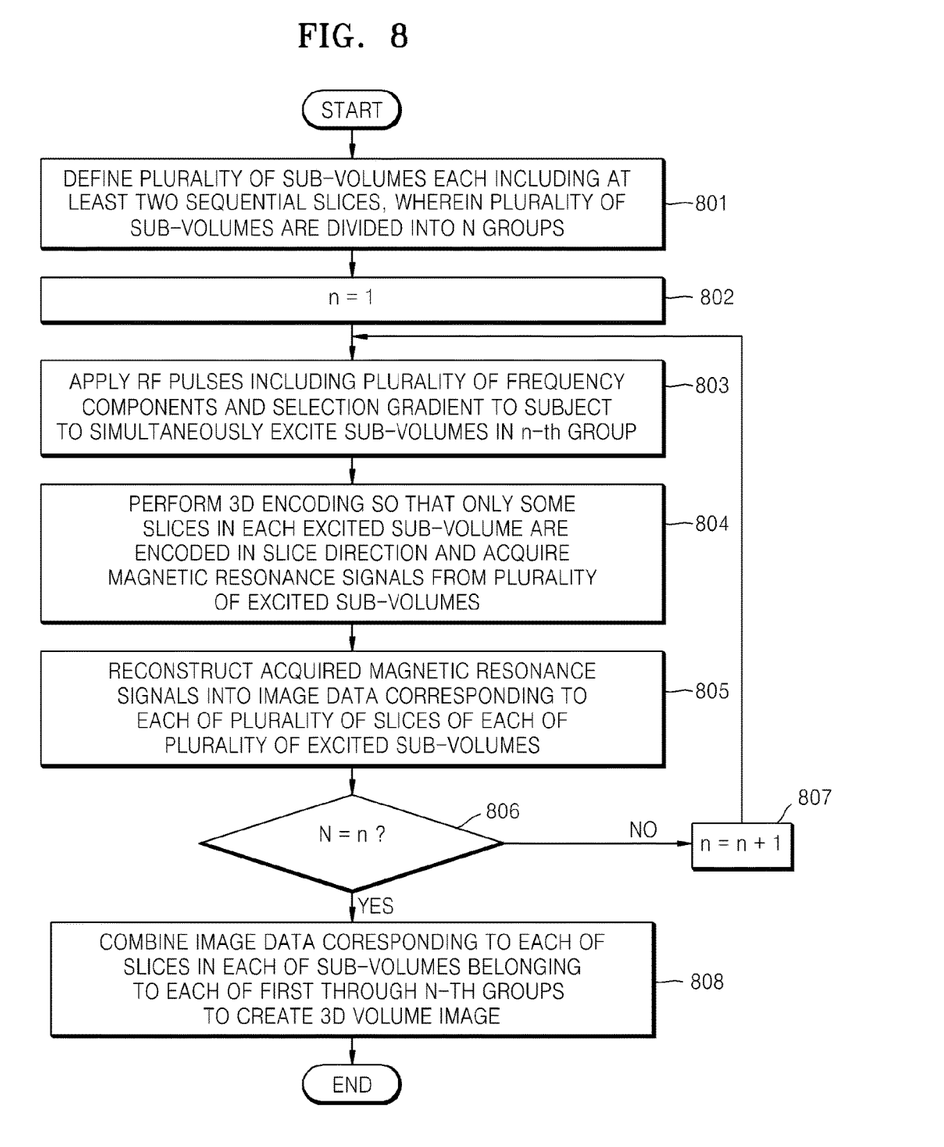
FIG. 8 is a flowchart of an example of an MRI method.

FIG. 8 is a flowchart of an example of an MRI method. Referring to FIG. 8, the MRI method includes operations performed in time series in the MRI system 100 of FIG. 1 or 5. Thus, the descriptions of the MRI system 100 with respect to FIGS. 1 and 5 are also applicable to the MRI method illustrated in FIG. 8.

Referring to FIGS. 1, 5, and 8, the MRI scanner 110 uses slices that make up a volume of a subject to define a plurality of sub-volumes so that each sub-volume includes at least two sequential slices (operation 801), wherein the plurality of sub-volumes are divided into N groups so that any neighboring sub-volumes belong to different groups. The controller 111 of the MRI scanner 110 then sets n=1 (operation 802). The MRI scanner 110 applies RF pulses including a plurality of frequency components and a selection gradient to the subject to simultaneously excite sub-volumes in the n-th group (operation 803). The RF driver 112 controls the RF coils 1142 to apply the RF pulses. The gradient driver 113 controls the gradient coils 1143 to apply the selection gradient.

The MRI scanner 110 performs 3D encoding on each of the excited plurality of sub-volumes so that only some of the slices in each of the excited plurality of sub-volumes are encoded in a slice direction, and acquires magnetic resonance signals from the excited plurality of sub-volumes (operation 804). For example, to perform the 3D encoding, the MRI scanner 110 may apply a first encoding gradient in a first direction and a second encoding gradient in a second direction to the subject. The second direction may be the same direction in which the selection gradient is applied in operation 803. The gradient driver 113 controls the gradient coils 1143 to apply the first and second encoding gradients. The second encoding gradient may be applied to encode only some of the slices in the second direction, i.e., in the slice direction.

The reconstructor 122 of the data processor 120 reconstructs the magnetic resonance signals acquired in operation 804 into image data corresponding to each of the plurality of slices of each of the excited plurality of sub-volumes (operation 805). The controller 111 of the MRI scanner 110 determines whether operations 803 through 805 have been performed for all of the N groups in the subject (operation 806). When operations 803 through 805 have not performed for all of the N groups in the subject, the method proceeds to operation 807. When operations 803 through 805 have been performed for all of the N groups, the method proceeds to operation 808.

The controller 111 increases n by 1 and proceeds to operation 803 (operation 807).

The synthesizer 124 fuses or combines image data corresponding to each of a plurality of slices in each of the plurality of sub-volumes belonging to each of the groups constituting the subject to create a 3D volume image (operation 808). All of the groups in the subject may be the first through N-th groups.

The MRI method of FIG. 8 facilitates creation of high-resolution 3D volume images at high speed.

The MRI systems 100 of FIGS. 1 and 5 and the MRI method of FIG. 8 use a multi-volume imaging technique that allows simultaneous excitation of a plurality of sub-volumes each including a plurality of slices, perform 3D gradient encoding in x-, y-, and z-axis directions to encode only some of the plurality of slices, and reconstruct images using coil sensitivity and RF decoding.

The MRI system 100, the MRI scanner 110, and the data processor 120 in FIG. 1 and the MRI system 100, the MRI scanner 110, the controller 111, the RF driver 112, the gradient driver 113, the magnet apparatus 114, the magnetic force generator 1141, the RF coils 1142, the gradient coils 1143, the signal acquisition unit 115, the data processor 120, the reconstructor 122, the synthesizer 124, the user interface 130, the input apparatus 132, and the display apparatus 134 in FIG. 5 described above that perform the operations illustrated in FIGS. 2A, 2B, 3, 4, and 6-8 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the detailed description.

What is claimed is:

1. A magnetic resonance imaging (MRI) method comprising:

dividing a volume of a subject into sub-volumes so that each of the sub-volumes comprises sequential slices, wherein the sub-volumes are assigned to groups so that adjacent sub-volumes belong to different groups;

applying radio-frequency (RF) pulses comprising frequency components and a selection gradient to the subject to excite the sub-volumes in each of the groups, wherein the sub-volumes in each group are excited simultaneously;

performing three-dimensional (3D) encoding on each the excited sub-volumes by selecting some slices for encoding in the slice direction from the sequential slices in each the excited sub-volume, and performing slice direction encoding on the slices selected for encoding;

acquiring magnetic resonance signals from the encoded sub-volumes; and reconstructing the acquired magnetic resonance signals into image data corresponding to each of the sequential slices in each of the encoded sub-volumes.

2. The method of claim 1, wherein the some slices are selected such that (1+v×fa)-th slices are selected from the sequential slices in each of the excited sub-volumes, wherein fa is a factor for satisfying the condition and is an integer greater than or equal to 1, and v is an integer that increases by 1 beginning from 0 until a value of (1+v×fa) reaches a number of the sequential slices in each of the excited sub-volumes.

3. The method of claim 1, wherein the reconstructing of the acquired magnetic resonance signals into the image data comprises:

reconstructing the acquired magnetic resonance signals into image data corresponding to each of the encoded sub-volumes; and reconstructing the image data corresponding to each of the encoded sub-volumes into the image data corresponding to each of the sequential slices in each of the encoded sub-volumes.

4. The method of claim 3, wherein the reconstructing of the acquired magnetic resonance signals into the image data corresponding to each of the encoded sub-volumes and the reconstructing of the image data corresponding to each of the encoded sub-volumes into the image data corresponding to each of the sequential slices in each of the encoded sub-volumes are performed based on channel information of multi-channel receiver coils configured to acquire the magnetic resonance signals.

5. The method of claim 1, wherein the groups comprise a first group through an N-th group, the sub-volumes are sequentially and cyclically distributed to the first group through the N-th group, and N is an integer greater than or equal to 2.

6. The method of claim 1, further comprising performing the applying of the RF pulses and the selection gradient to the subject, the performing of the 3D encoding on each of the excited sub-volumes, the acquiring of the magnetic resonance signals from the encoded sub-volumes, and the reconstructing of the acquired magnetic resonance signals into image data for all of the groups to obtain reconstructed image data for all of the groups; and synthesizing the reconstructed image data for all of the groups.

7. A non-transitory computer-readable storage medium storing instructions that, when executed by a processor, cause the processor to perform the method of claim 1.

8. A medical resonance imaging (MRI) method comprising:

applying a pulse sequence to a subject, the pulse sequence comprising a slice direction encoding gradient, to encode some slices of sequential slices included in each sub-volume of sub-volumes that constitute a volume of the subject, wherein the sub-volumes are assigned to groups so that adjacent sub-volumes belong to different groups;

reconstructing image data corresponding to each of the slices in each of the sub-volumes of one of the groups;

applying the pulse sequence and performing the reconstructing of the image data for all of the groups; and in response to determining that the applying of the pulse sequence and the reconstructing of the image data have been performed for all of the groups, combining image data corresponding to each of the slices in each of the sub-volumes of each of the groups to create a three-dimensional (3D) volume image of the subject.

9. The method of claim 8, wherein the reconstructing of the image data comprises:

reconstructing acquired magnetic resonance signals acquired from the encoded sub-volumes into image data corresponding to each of the sub-volumes; and reconstructing the image data corresponding to each of the sub-volumes into image data corresponding to each of the sequential slices in each of the sub-volumes of the one group.

10. The method of claim 9, wherein the reconstructing of the acquired magnetic resonance signals into the image data corresponding to each of the sub-volumes and the reconstructing of the image data corresponding to each of the sub-volumes into the image data corresponding to each of the sequential slices in each of the sub-volumes of the one group are performed based on channel information of multi-channel receiver coils configured to acquire the magnetic resonance signals.

11. A non-transitory computer-readable storage medium storing instructions that, when executed by a processor, cause the processor to perform the method of claim 8.

12. A magnetic resonance imaging (MRI) system comprising:

an MRI scanner configured to:

divide a volume of a subject into sub-volumes so that each of the sub-volumes comprises sequential slices, wherein the sub-volumes are assigned to groups so that adjacent sub-volumes belong to different groups, apply radio-frequency (RF) pulses comprising frequency components and a selection gradient to the subject to excite the sub-volumes in each of the groups, wherein the sub-volumes in each group are excited simultaneously, perform three-dimensional (3D) encoding on each of the excited sub-volumes by selecting some slices for encoding in the slice direction from the sequential slices in each of the excited sub-volumes, and performing slice direction encoding on the slices selected for encoding, and acquire magnetic resonance signals from the encoded sub-volumes; and a data processor configured to reconstruct the acquired magnetic resonance signals into image data corresponding to each of the sequential slices in each of the encoded sub-volumes.

13. The system of claim 12, wherein the sequential slices are selected such that (1+v×fa)-th slices are selected from the sequential slices in each of the excited sub-volumes, wherein fa is a factor for satisfying the condition and is an integer greater than or equal to 1, and v is an integer that increases by 1 beginning from 0 until a value of (1+v×fa) reaches a number of the sequential slices in each of the excited sub-volumes.

14. The system of claim 12, wherein the data processor is further configured to:
   reconstruct the acquired magnetic resonance signals into image data corresponding to each of the encoded sub-volumes; and
   reconstruct the image data corresponding to each of the encoded sub-volumes into image data corresponding to each of the sequential slices in each of the encoded sub-volumes.

15. The system of claim 14, wherein the reconstructing of the acquired magnetic resonance signals into the image data corresponding to each of the encoded sub-volumes and the reconstructing of the image data corresponding to each of the encoded sub-volumes into the image data corresponding to each of the sequential slices in each of the encoded sub-volumes are performed based on channel information of multi-channel receiver coils configured to acquire the magnetic resonance signals.

16. The system of claim 12, wherein the MRI scanner comprises gradient coils configured to apply a first encoding gradient in a first direction, a second encoding gradient in a second direction, and a frequency encoding gradient in a third direction to the subject to perform the 3D encoding on each of the excited sub-volumes;
   the second direction is the slice direction; and
   the second encoding gradient encodes only the some slices of the sequential slices in each of the excited sub-volumes.

17. The system of claim 12, wherein the MRI scanner is further configured to perform the applying of the RF pulses and the selection gradient to the subject, the performing of the 3D encoding on each of the excited sub-volumes, and the acquiring of the magnetic resonance signals from the excited sub-volumes to obtain magnetic resonance signals for all of the groups; and
   the data processor comprises:
   a reconstructor configured to perform the reconstructing of the acquired magnetic resonance signals into image data corresponding to each of the sequential slices in each of the encoded sub-volumes for all of the groups to obtain reconstructed image data for all of the groups; and
   a synthesizer configured to synthesize the reconstructed image data for all of the groups.

\* \* \* \* \*